US00PP11592P

United States Patent [19]

Jelenkovic et al.

[11] Patent Number: Plant 11,592

[45] Date of Patent: Oct. 24, 2000

[54] STRAWBERRY PLANT NAMED 'NJ8607-2'

[75] Inventors: Gojko L. Jelenkovic, Piscataway; Joseph A. Fiola, Whiting, both of N.J.

[73] Assignee: Rutgers University, New Brunswick, N.J.

[21] Appl. No.: 09/034,040

[22] Filed: Mar. 3, 1998

[51] Int. Cl.[7] ..... A01H 5/00

[52] U.S. Cl. ..... Plt./208

[58] Field of Search ..... Plt./208

[56] References Cited

U.S. PATENT DOCUMENTS

P.P. 4,574 7/1980 Johnson, Jr. ..... Plt./208

P.P. 7,160 2/1990 Johnson, Jr. et al. ..... Plt./208

*Primary Examiner*—Howard J. Locker
*Assistant Examiner*—Wendy A. Baker
*Attorney, Agent, or Firm*—Synnestvedt & Lechner LLP

[57] ABSTRACT

A new and distinct cultivar of strawberry plant (*Fragaria*× *ananassa*) named 'NJ8607-2', which is a short day cultivar similar to 'Earliglow', but which is exceptional for its early season harvest of very attractive large fruit, good shelf-life, and high productivity, combined with good horticultural qualities and good disease resistance. The plant is well adapted to matted-row, ribbon-row, and high density planting systems, and performs consistently in diverse environments. The fruit size is larger than that of 'Earliglow', the major cultivar in its season.

4 Drawing Sheets

BACKGROUND OF THE NEW PLANT

The present invention relates to the discovery and asexual propagation of a new and distinct short day type cultivar of strawberry plant (*Fragaria*×*ananassa*), which resulted from crossing the advanced selection 'MDUS5347' as the seed parent and the advanced selection 'NJ8224-3' as the pollen parent in 1986 at the Rutgers University Plant Science Greenhouses in New Brunswick, N.J. Both parent plants are unpatented, non-commercial varieties. The complete pedigree of 'NJ8607-2' is shown below:

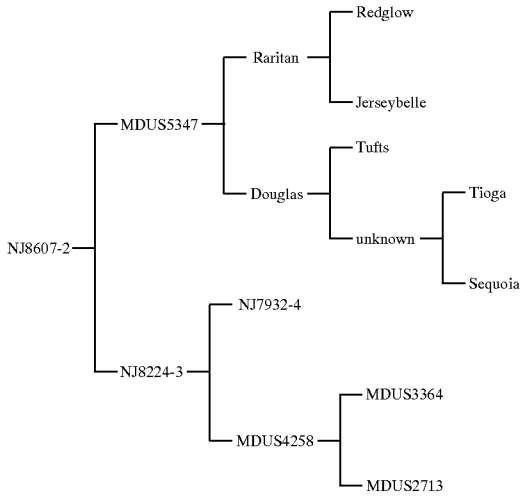

The new cultivar has been designated as 'NJ8607-2'. This specific clone was the second of two selections in the progeny, and was discovered by Gojko L. Jelenkovic in June, 1988 at Rutgers Plant Science Farm 3 in New Brunswick, N.J. The new 'NJ8607-2' plant was recognized as being distinguishable from other known early strawberry plant varieties in that it demonstrates a longer shelf life than those other varieties.

The new plant was designated 'NJ8607-2' in the breeding records and was first asexually propagated, by runners, by Gojko L. Jelenkovic and Joseph A. Fiola in about July, 1988 at Rutgers Plant Science Farm 3 in New Brunswick, N.J. It was recognized and selected as a distinctive and superior clone by Joseph A. Fiola based on extensive testing at the Rutgers Fruit Research and Extension Center in Cream Ridge, N.J. Limited grower testing started in 1994 . The new cultivar has shown to be stable in its distinguishing characteristics over several genertions, through successive asexual propagations using runners.

DETAILED BOTANICAL DESCRIPTION OF THE NEW PLANT

Figure 1:
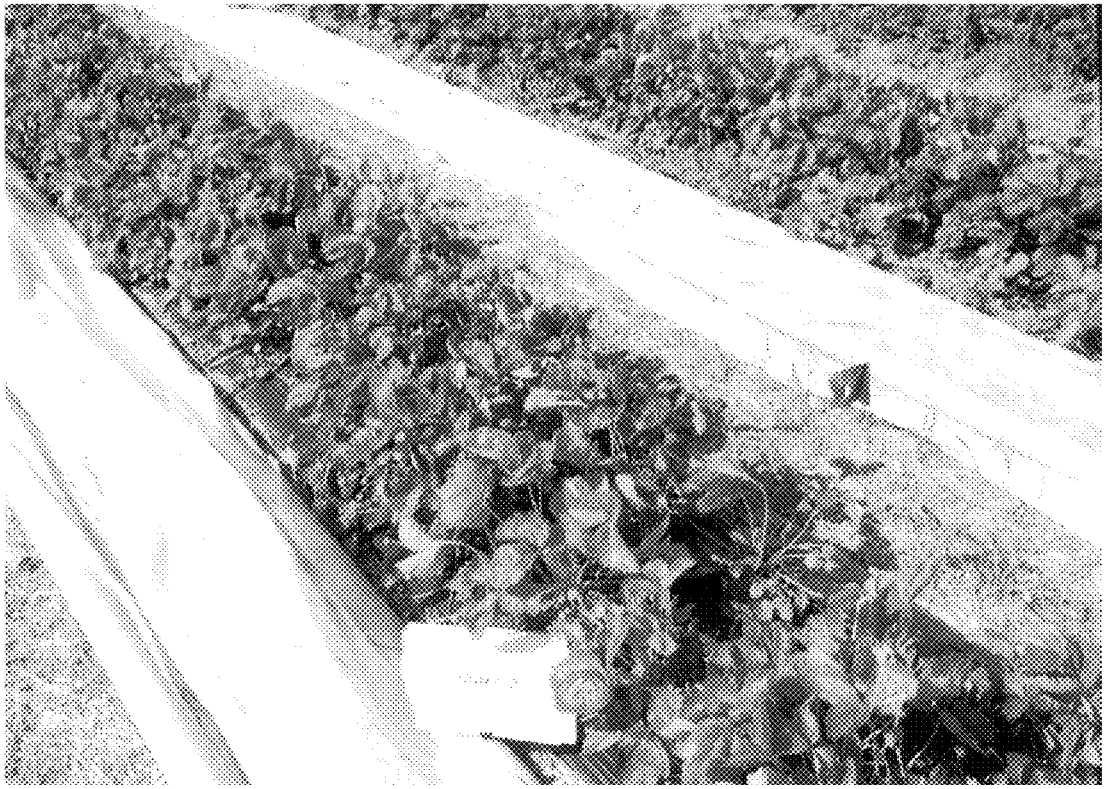
FIG. 1 illustrates a typical example of a plot of the new cultivar, illustrating the vegetative habit in a high density plasticulture system.
Figure 2:
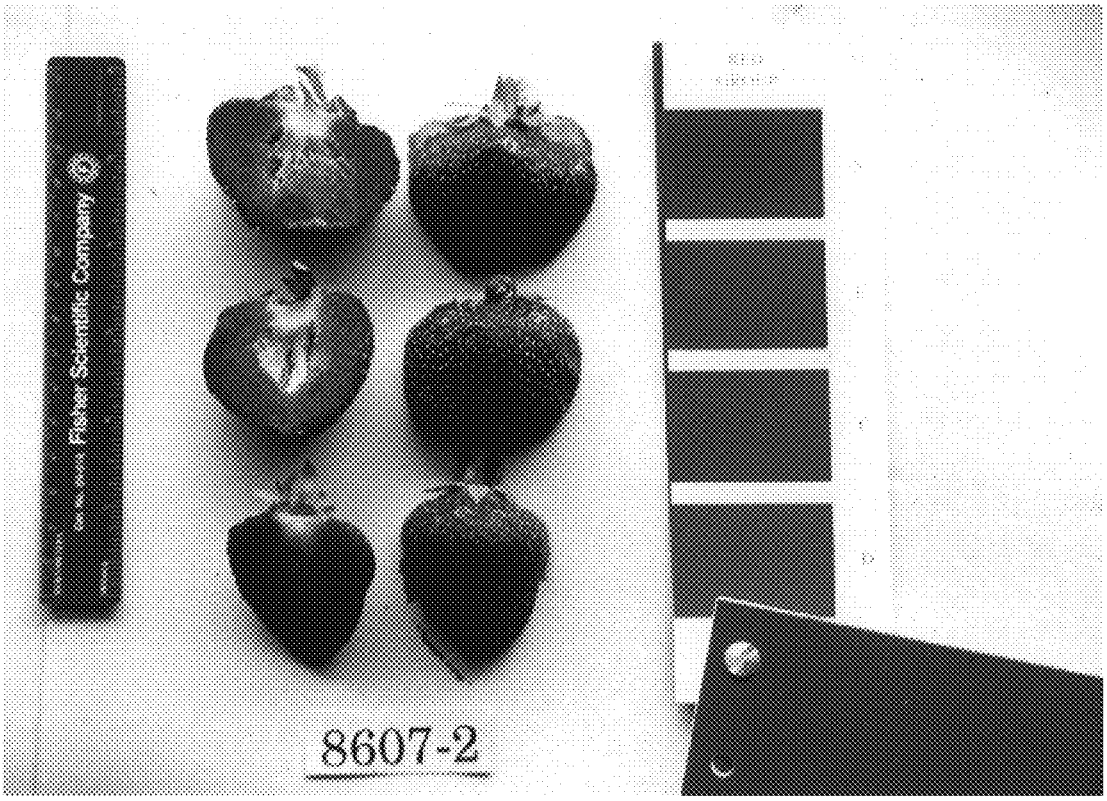
FIG. 2 shows a typical example of the strawberry fruit of the new variety, disclosing the fruit's conic shape, length, width, external flesh and skin color, intenal flesh color, seed color and prominence, and calyx size and pose.
Figure 3:
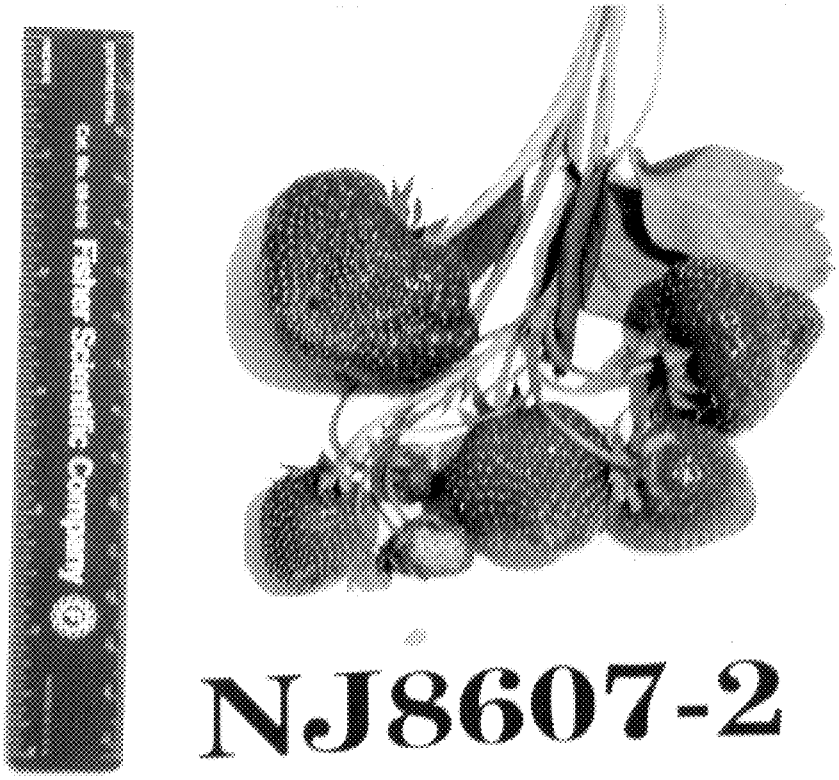
FIG. 3 depicts a raceme of the fruit of the new cultivar, with reference to a 6-inch (15 cm.) ruler.
Figure 4:
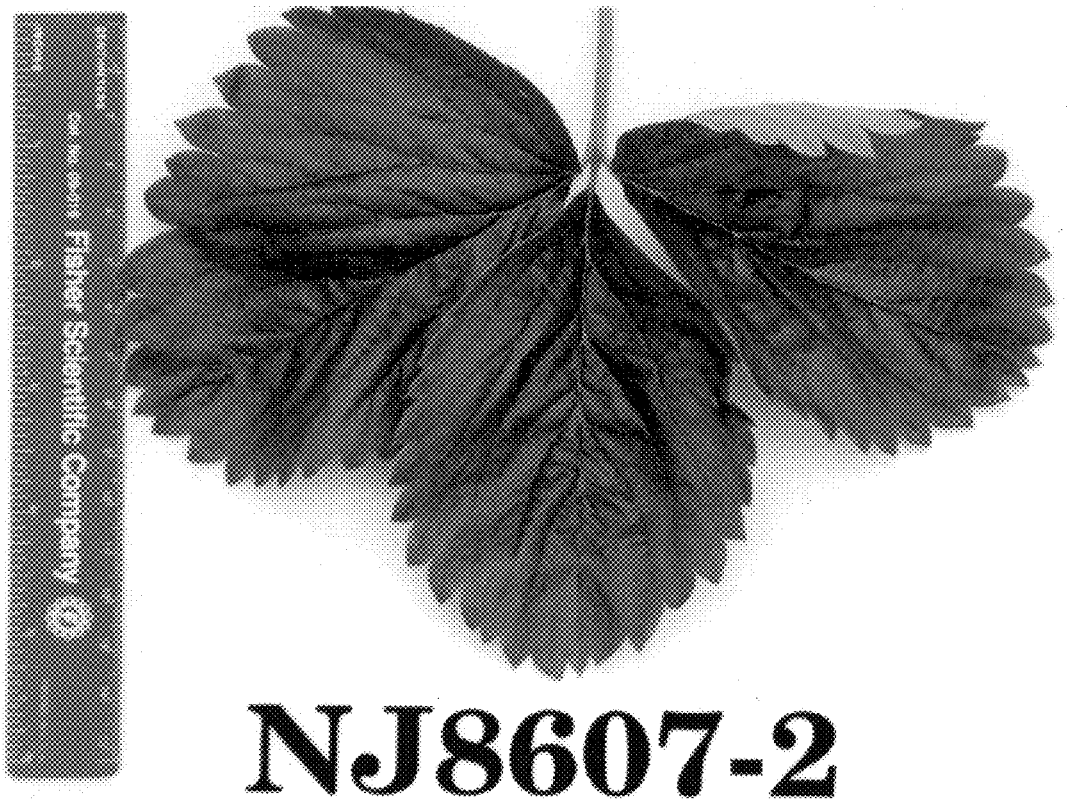
FIG. 4 illustrated a typical trifoliate leaf of the new cultivar, with reference to a 6-inch (15 cm.) ruler.

The following detailed description of the new 'NJ8607-2' plant is based upon observation made of the plants grown in Cream Ridge, N.J., during about the month of April through June. It is believed that this description will apply to 'NJ8607-2' cultivar plants grown in similar conditions of soil and climate elesewhere.

Throughout this specification, color names beginning with a small letter signify that the name of that color as used in common speech is aptly descriptive. Color names beginning with a capital letter designate color values based on the R.H.S. Colour Chart published by The Royal Horticultural Society of London, England.

Plants and foliage: The vegetative habit is one of high overall vigor, with branching and runnering to form a medium to high density matted-row. It produces many medium sized crowns when planted in high density on plastic. It has also performed well in ribbon-row culture.

The plant appears to be generally well adapted to, and has performed very well on, both the light, sandy soils in Southern New Jersey, as well as the heavier soils in the northern locations of New Jersey.

The trifoliate leaves are semi-erect to erect, petioles bearing scattered hirsute hairs; 8 leaflets ovate-orbicular, margins serrate, apices round, bases of terminal leaflets cuneate and 2 lateral leaflet bases strongly oblique; upper leaflet surface lightly and scattered sericeous; lower leaflet surface lightly and scattered sericeous hairs on and between the veins; all leaflet hairs appressed; petiolules lightly hirsute. Adaxial and abaxial leaf surfaces are medium green in coloration and typical of the species. Typical measurements for trifoliate leaves are shown in table 6.

Isozymes in leaf extracts: Isozyme patterns for glucose phosphate isomerase (GPI), leucine amino peptidase (LAP), and phosphoglucomutase (PGM) show banding patterns for this genotype (Table 5 ).

Disease and pest reaction: The foliage has good leaf spot and leaf scorch resistance, and will tolerate powdery mildew. The plant has been screened for resistance against strains A-1, A-3, A-4 and A-6 of Phytophthora, which causes red stele. The plants have also shown good field resistance to Verticillium wilt.

Flowering, fruit, and production characteristics: The plant flowers over a short period with the majority of flowers opening about the same time as the known (unpatented) 'Earliglow 'variety, about last week in April. Flowers are white in coloration and typical of the species. Fruit are numerous, large, and borne on medium length, branching trusses. In particular, the inflorescence is branching with the primary peduncle (range 85–100 mm) branching to a secondary peduncle (range 55–65 mm) which supports the primary fruit and a group of pedicels (range 25–50 mm) supporting the secondaries, tertiaries, etc.

The strawberry fruit is attractive, intensely colored, with medium-to-high gloss. Primary fruit are large, with secondary and tertiary fruit maintaining relatively good commercial size. The largest individual primaries of a harvest can weigh in excess of 40 grams/fruit. Large primaries tend to be slightly irregular in shape; the shape is flat conic, with the width about double the height. Seed ripen from green to tan, typical of the species, and about one half of the seed width is raised above the berry surface. The calyx typically is about 10.5 mm in diameter, and green in color, typical of the species and starts even with the top of the berry (no shoulder), and lays flat on the berry.

The berry skin has good abrasion resistance and the flesh is firm. The berry color is deep red (Red 53A; Red 59A when overripe). The internal color grades from Red 42A on the outside to Red 42C towards the center, when overripe it is a uniform 59A. The fruit has good overall eating quality, tending toward high acid/sugar ratio, and high strawberry flavor intensity. The berry has excellent shelf-life, maintaining gloss, color, firmness, and flavor for 5–7 days in storage.

TABLE 1

Yield parameters of 'NJ8607-2', relative to other cultivars and selections of the early harvest season, in a matted-row production system at Cream Ridge, New Jersey; data is combined means of 1991 and 1992.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| NJ8607-2 | 6 | 75 | 2170 | 10880 | 17.3 | 12.5 |
| NJ8608-1 | 7 | 55 | 1160 | 8720 | 16.4 | 13.8 |
| NJ8614-2 | 7 | 65 | 1060 | 10470 | 16.4 | 12.5 |
| Earliglow | 7 | 80 | 1390 | 11970 | 14.0 | 9.5 |
| Raritan | 6 | 85 | 610 | 11880 | 16.7 | 13.0 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 2

Yield parameters of 'NJ8607-2', relative to other cultivars and selections of the early harvest season, in a matted-row production system at Cream Ridge, New Jersey; data is combined means of 1994 and 1995.

| | Plant | | Yield | | Berry Wt.** | |
|---|---|---|---|---|---|---|
| Genotype | Bed | Vig* | Early (lb/A) | Total (lb/A) | Prim*** (g) | Avg (g) |
| NJ8607-2 | 6 | 75 | 1590 | 11046 | 16.5 | 12.2 |
| NJ8608-1 | 7 | 55 | 1350 | 8610 | 13.9 | 11.6 |
| NJ8614-2 | 7 | 65 | 1100 | 9170 | 16.3 | 12.9 |
| Earliglow | 7 | 80 | 2280 | 9400 | 11.8 | 9.6 |
| Raritan | 6 | 85 | 740 | 5350 | 14.0 | 11.0 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 3

Yield parameters of 'NJ8607-2', relative to other cultivars and selections of the early harvest season, in a plasticulture system at Cream Ridge, New Jersey; data is combined means of 1994 and 1995.

| | | Yield | | Berry Wt.** | |
|---|---|---|---|---|---|
| Genotype | Plant Vig* | Early (lb/A) | Total (lb/A) | Prim*** (g) | Avg (g) |
| NJ8826-11 | 67 | 1440 | 6960 | 14.5 | 11.0 |
| NJ8607-2 | 65 | 660 | 6110 | 14.1 | 11.4 |
| NJ8608-1 | 63 | 760 | 6940 | 13.1 | 10.1 |
| NJ8614-2 | 65 | 740 | 7530 | 15.7 | 12.3 |
| Chandler | 79 | 330 | 9790 | 14.2 | 11.5 |

*Plant vigor ratings are determined through a rating of the vigor of the plant on a subjective scale of 10 (plant extremely weak) to 90 (plant strong, vigorous, filling in predetermined production area).
**Data obtained by weighing a random selection of 20 fruit from a plot at each harvest.
***Refers to the primary or first harvested berries.

TABLE 4

Mean berry length (L), width (W), and girth (G) for 'NJ8607-2' and other cultivars; data from 1995.

| Genotype | Length (mm) | Width (mm) | Girth (mm) |
|---|---|---|---|
| NJ8607-2 | 35 | 37 | 31 |
| NJ8826-11 | 40 | 47 | 40 |
| NJ8614-2 | 36 | 39 | 26 |
| NJ8608-1 | 43 | 37 | 33 |
| NJ8944-1 | 45 | 47 | 40 |
| Chandler | 37 | 35 | 28 |

TABLE 5

Isozymes patterns for leaf extracts for glucose phosphate isomerase (GPI), leucine amino peptidase (LAP), and phosphoglucomutase (PGM)

| Genotype | GPI | LAP | PGM |
|---|---|---|---|
| NJ8826-11 | A6 | B3 | C2 |
| NJ8614-2 | A1 | B3 | C3 |
| NJ8607-2 | A1 | B3 | C3 |
| Chandler | A1 | B3 | C1 |

TABLE 6

Typical measurements for length and width of trifoliate leaves of 'NJ8607-2'

| | 1° leaf | | 2° leaves | |
|---|---|---|---|---|
| | Length (mm) | Width (mm) | Length (mm) | Width (mm) |
| Average | 80 | 55 | 75 | 75 |
| Range: | | | | |
| high | 87 | 75 | 84 | 80 |
| low | 65 | 60 | 55 | 65 |

We claim:

1. A new and distinct strawberry plant named 'NJ8607-2', as herein illustrated and described.

* * * * *